United States Patent
Shukla et al.

(10) Patent No.: US 10,001,436 B2
(45) Date of Patent: Jun. 19, 2018

(54) IN-SITU MEASUREMENT OF CORROSION IN BURIED PIPELINES USING VERTICALLY MEASURED PIPE-TO-SOIL POTENTIAL

(71) Applicant: Southwest Research Institute, San Antonio, TX (US)

(72) Inventors: Pavan K. Shukla, San Antonio, TX (US); Biswajit Dasgupta, Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 682 days.

(21) Appl. No.: 14/161,165

(22) Filed: Jan. 22, 2014

(65) Prior Publication Data

US 2015/0204775 A1    Jul. 23, 2015

(51) Int. Cl.
*G01N 17/00* (2006.01)
*G01N 17/04* (2006.01)

(52) U.S. Cl.
CPC ........... *G01N 17/006* (2013.01); *G01N 17/04* (2013.01)

(58) Field of Classification Search
None
See application file for complete search history.

(56) References Cited

U.S. PATENT DOCUMENTS

| | | | | |
|---|---|---|---|---|
| 2,378,440 A | * | 6/1945 | Scott | E02D 1/00 172/300 |
| 2,607,218 A | * | 8/1952 | Hansen | E02D 1/022 346/113 |
| 4,078,510 A | * | 3/1978 | Morgan | C23F 13/04 114/144 A |
| 4,409,080 A | * | 10/1983 | Slough | C23F 13/04 204/196.06 |
| 4,581,497 A | * | 4/1986 | Morrison | B65H 75/38 191/12.2 R |
| 4,995,168 A | * | 2/1991 | Shiner | G01V 1/38 116/209 |
| 6,060,877 A | * | 5/2000 | Nekoksa | G01N 17/02 204/196.06 |

(Continued)

FOREIGN PATENT DOCUMENTS

FR    2355285 A1  *  1/1978  ............. G01N 17/02

OTHER PUBLICATIONS

Whitham D. Reeve, "Principles and Practice of Earth Electrode Measurements", Rev. 1.1, Aug. 1, 2008.*

(Continued)

*Primary Examiner* — Alexander Satanovsky
*Assistant Examiner* — Brent A Fairbanks
(74) *Attorney, Agent, or Firm* — Livingston Law Firm

(57) ABSTRACT

A method for in-situ measuring the corrosion rate of a corroding site on an underground metal structure buried in soil, the structure being under cathodic protection. The structure-to-soil potential at varying depths above the pipeline is measured to a depth above, but not reaching the structure. These measurements are extrapolated to obtain data representing the structure-to-soil potential at the surface of the structure under the probe. The gradient of the electrical potential at this surface is used to calculate the corrosion rate of the defect. A special probe may be used to obtain the potential measurement data.

5 Claims, 3 Drawing Sheets

(56) References Cited

U.S. PATENT DOCUMENTS

| | | | |
|---|---|---|---|
| 8,310,243 B2 | 11/2012 | Shukla et al. | |
| 9,128,019 B2* | 9/2015 | Wayman | F17D 5/00 |
| 2003/0169058 A1* | 9/2003 | Pierre | G01N 17/02 |
| | | | 324/700 |
| 2004/0201381 A1* | 10/2004 | Murray | E21B 10/58 |
| | | | 324/522 |
| 2012/0038376 A1* | 2/2012 | Shukla | G01N 17/02 |
| | | | 324/700 |

OTHER PUBLICATIONS

Whitham D. Reeve, "Principles and Practice of Earth Electrode Measurements", Rev. 1.1, Aug. 1, 2008.*

* cited by examiner

IN-SITU MEASUREMENT OF CORROSION IN BURIED PIPELINES USING VERTICALLY MEASURED PIPE-TO-SOIL POTENTIAL

TECHNICAL FIELD OF THE INVENTION

This invention relates to detection and in-situ measurement of corrosion on buried pipelines (or other corrodible buried structures), and more particularly to using measurements of pipe-to-soil potential for such purposes.

BACKGROUND OF THE INVENTION

Buried pipelines are often coated and/or subjected to cathodic protection techniques in an effort to mitigate corrosion. Cathodic protection may be achieved by electrically connecting the pipeline to another more easily corroded metal to act as the anode of a simulated electrochemical cell. Another type of cathodic protection technique uses impressed currents; a current is applied to the pipeline to force the pipeline surface to act as a cathode.

However, even the best of today's corrosion avoidance techniques do not prevent corrosion at some point. In the pipeline industry, defects in the pipeline coating are known as "holidays", and result in the metal surface of the pipeline being exposed to the soil. Furthermore, coatings can degrade and exfoliate, creating areas where the coating material is present but partially or wholly disbonded from the pipe, limiting protection from corrosion.

Knowledge of in-situ corrosion rates at holidays and disbonded coating sites is important to integrity management of buried pipelines. However, buried pipelines are not easily accessible for corrosion detection. Thus, special techniques have been developed for detecting coating defects and other corrosion without need to expose the pipe surface.

DETAILED DESCRIPTION OF THE INVENTION

As stated in the Background, buried structures present particular problems for corrosion detection. Although the following description is in terms of detecting corrosion on a coated surface of a pipeline, the same concepts can be applied to detecting corrosion defects in any corrodible buried structure. The "corrodible" characteristic of the pipeline or buried structure means that at least a portion of its surface area is susceptible to metallic corrosion. The structure may be coated or uncoated, with "coated" referring to having paint or other covering material designed to protect the structure against corrosion.

The pipeline (or other structure) is assumed to be buried in soil. The term "soil" is used in a most general sense to mean any covering material, typically earth having some degree of moisture.

The following description is directed to in-situ corrosion rate estimation using vertically measured pipe-to-soil potentials over a buried pipeline under cathodic protection. The method detects pipeline coating defects, including defects known as "holidays" in the industry, as well as disbondment sites. The method may be performed for any location of interest on the pipeline.

As explained below, pipe-to-soil potential is measured vertically, starting from the ground surface and downwardly approaching a surface of interest on the buried pipeline. The measurements are conducted using a special pipe-to-soil potential measurement device inserted in the soil above the pipeline. The pipe-to-soil potential data is used to calculate corrosion rate at that location on the pipeline.

Figure 1:
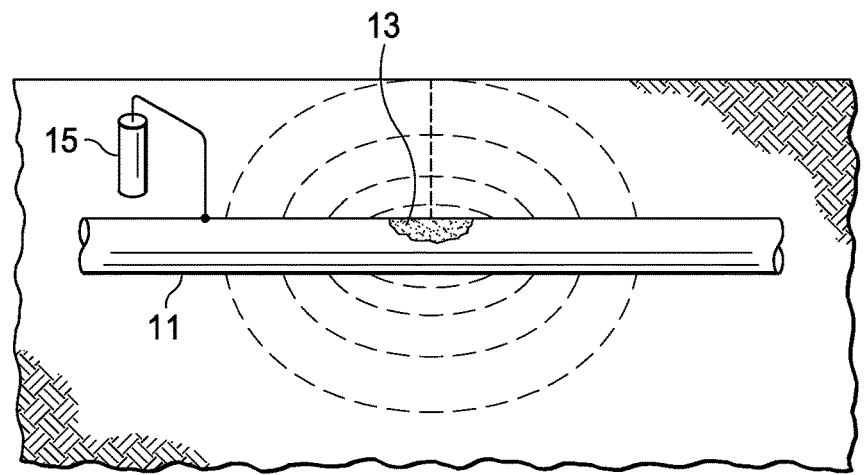
FIG. 1 illustrates the theoretical basis of detecting, from vertically measured pipe-to-soil potential, corrosive defects on the surface of a buried pipeline under cathodic protection.

FIG. 1 is a schematic view of a buried pipeline 11 under cathodic protection. The pipeline 11 is shown as having a defect 13 in its coating. It should be understood that the invention will also work for corroding sites on uncoated pipelines under cathodic protection.

The cathodic protection is being used to control the corrosion of the pipeline by causing the pipeline to act as a cathode of an electrochemical cell. The pipeline 11 is connected to a more easily corroded "sacrificial" metal, which acts as the anode 15. The sacrificial anode 15 then corrodes instead of the protected metal of the pipeline. For some structures, where galvanic cathodic protection is not adequate, an external DC electrical power source may be used to provide sufficient current. The method described herein is suitable for use with both galvanic and impressed-current protected pipelines.

When a pipeline is subjected to cathodic protection, a current-potential distribution develops in the soil environment near the pipeline. This current-potential distribution is a result of charge flow between the anode 15 and the pipeline 11. The magnitude and distribution of the charge flow is considerably different near defect sites than at properly coated surfaces of the pipe. This affects current and potential distribution in the soil near the defect sites.

FIG. 1 further illustrates how the in-situ corrosion rate measurement method described herein may be based on measurement of this current-potential distribution. An area on the surface of a pipeline having a coating defect, such as defect 13, will generate an electrical current and potential distribution in the neighboring soil environment. This potential distribution is represented by the iso-potential curves of FIG. 1. The characteristic potential distribution will be superposed to the potential distribution generated by the cathodic protection system.

The dotted vertical line illustrates where pipe-to-soil potential measurements can be conducted. Obtaining these measurements would involve drilling a 4-6 inch diameter hole downward into the soil along the vertical line. The corrosion rate of a defect can be estimated if pipe-to-soil potentials with respect to a reference electrode are measured vertically from the ground surface toward a suspected site on the pipeline.

Pipe-to-Soil Measurement Probe

Figure 2:
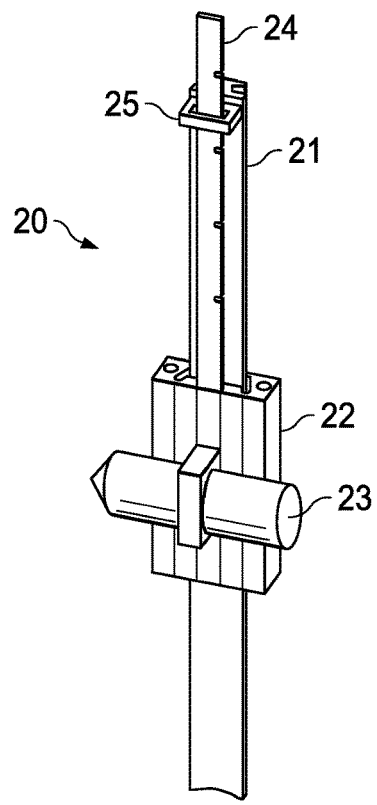
FIG. 2 illustrates a probe used for making vertical pipe-to-soil potential measurements.

FIG. 2 illustrates a probe 20 to be inserted into a hole drilled into the ground above a location of interest on the pipeline, as shown in FIG. 1. The hole is drilled such that its axis is perpendicular, or close to perpendicular, to the location of interest.

Probe 20 has a rail 21, slider 22, reference electrode 23, and sliding ruler 24. Connection cables, not shown in FIG. 2, are used in operation as explained below. Typically, rail 21 is of sufficient length to rest in the bottom of the drilled hole into which it is placed during use. Rail 21 may be any thin rigid length of material; its main function is to provide a track upon which slider 22 may move up and down.

Slider 22 includes a movable latching mechanism that allows it to be secured, released, re-positioned and re-secured along rail 21. Slider 22 may be any mechanism that holds electrode 23 and allows it to slide and be temporarily secured at varying positions up and down rail 21.

As explained below, the pipe-to-soil measurements call for slider 22 to be re-positioned at varying depths within a hole over a pipeline. Various means can be used to re-position slider 22 on rail 21 when probe 20 is operation. Although not necessary, ideally, slider 22 will be capable of being repositioned without removing probe 20 from the hole. Various manual or automated re-positioning mechanisms can be devised.

Reference electrode 23 is used to make pipe-to-soil potential measurements. An example of a suitable material for reference electrode 23 is Cu/saturated $CuSO_4$.

Sliding ruler 24 is used to measure the depth of the reference electrode 23 from the ground surface. As slider 22 moves up and down, so does ruler 24 by a corresponding amount, so that the depth of reference electrode 23 during a particular pipe-to-soil potential measurement can be measured. A bracket 25 may be used to hold ruler 24 along a vertical track adjacent rail 21.

Pipe-to-Soil Potential Measurement

Figure 3:
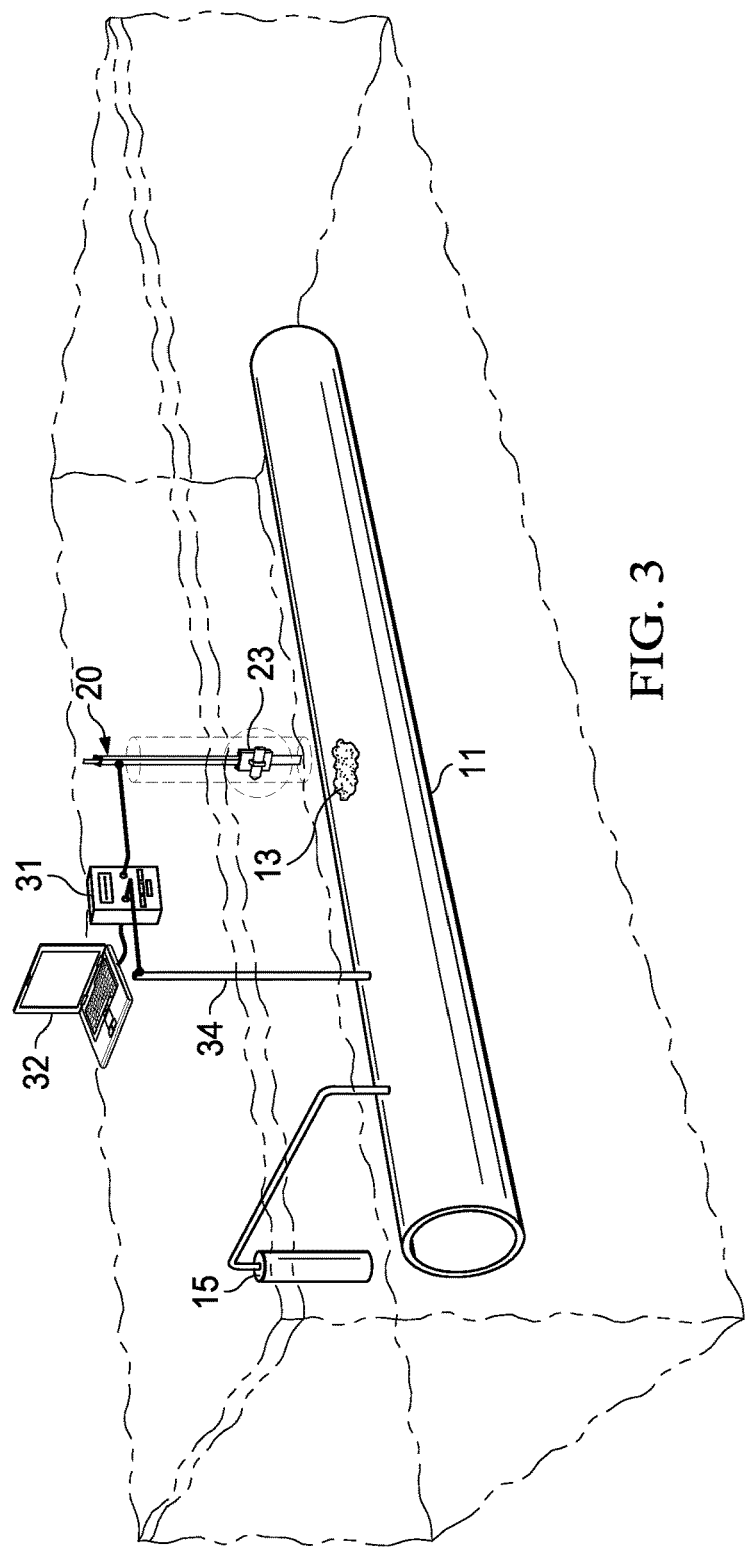
FIG. 3 illustrates a system, incorporating a probe such as the probe of FIG. 2, for detecting corrosion.

FIG. 3 illustrates probe 20 inserted into a hole drilled above a pipeline 11 above a location of interest on the pipeline. The above-described probe 20 is especially suitable for measurements, but other probes can be imagined that allow measurement of pipe-to-soil potential at various depths in a vertical direction above a location of interest on a pipeline.

As in FIG. 1, pipeline 11 is under cathodic protection with a sacrificial anode 15 buried near the pipeline. Pipeline 11 has a defect 13, such that an electrical potential distribution exists in the soil near the defect.

The placement of probe 20 exactly over a defect 13 is illustrative. In practice, probe 20 may or may not detect a defect, which may or may not be directly under the probe. The logistics of using probe 20 may vary widely. For example, probe 20 may be used in a methodical manner to monitor the corrosion status of a pipeline, with holes being drilled at regular intervals. The probe may be moved across the ground, into a series of holes over the pipeline, to collect data at different locations on the pipeline. Alternatively, holes may be dug and probes left in place for permanent monitoring. Or, probe 20 may be used sporadically, inserted into holes drilled at one or more locations of particular interest over a pipeline.

The hole into which probe 20 is placed has sufficient width so that slider 23 can be moved up and down within the hole. The depth of the hole depends on the depth of the pipeline. In general, the hole will terminate well above the top surface of the pipeline.

A feature of probe 20 is that it need not touch the pipeline, and thus the hole into which it is inserted need not be dug close to the pipeline. Drilling a hole close to the pipeline could be a safety concern and may damage the pipeline. Furthermore, if a probe were required to be placed very close to the pipeline, it could cause unintended damage to the surface of the pipeline. In addition, placement of the probe 20 too close to the pipe surface could cause disruption of charge flow originating from the location of interest on the pipeline. For these reasons, the pipe-to-soil potential measurements are conducted from the ground surface up until a safe distance from the pipeline, typically within a range of 0.5 to 1 foot above the top surface of the pipeline.

In operation, probe 20 is electrically connected to a voltage measuring device (voltmeter) 31. A second electrical connection is made to the metal of pipeline 11, typically via a riser 34. This second connection is spaced from the reference electrode, with the assumption being that the metal potential at the point of this second contact is the same as at the location of measurement. Risers 34 are commonly found on pipelines, but other means of electrically connecting voltmeter 32 to the metal of pipeline may be used.

Voltmeter 31 measures the pipe-to-soil potential relative to a selected position of reference electrode 23.

An analysis unit 32 is used to receive measurement data from voltmeter 31. It also has appropriate hardware and software to process the measurement data to perform the corrosion rate estimation calculations described herein. More specifically, it is programmed to extrapolate measured pipe-to-soil potential data from a depth at which data is actually acquired to a depth at the surface of the pipe, as described below. It further uses the extrapolated data to estimate the corrosion rate of a defect, if any, at the location of interest. Analysis unit 32 may be on-site or may be remote, with any one of various data communications techniques used to receive measurement data from voltmeter 31.

The above method is described in terms of "pipe-to-soil" potential, with an electrical connection to the pipeline, However, other "soil-to-soil" potential methods could be devised in which one electrical connection of the voltmeter is made to ground (soil) rather than to the pipeline. The other connection is made to probe 20 as described. For example, if the pipe-to-soil potential of the pipeline is previously measured or otherwise known, the calculations described below can be modified accordingly.

Extrapolation of Measurement Data

Figure 4:
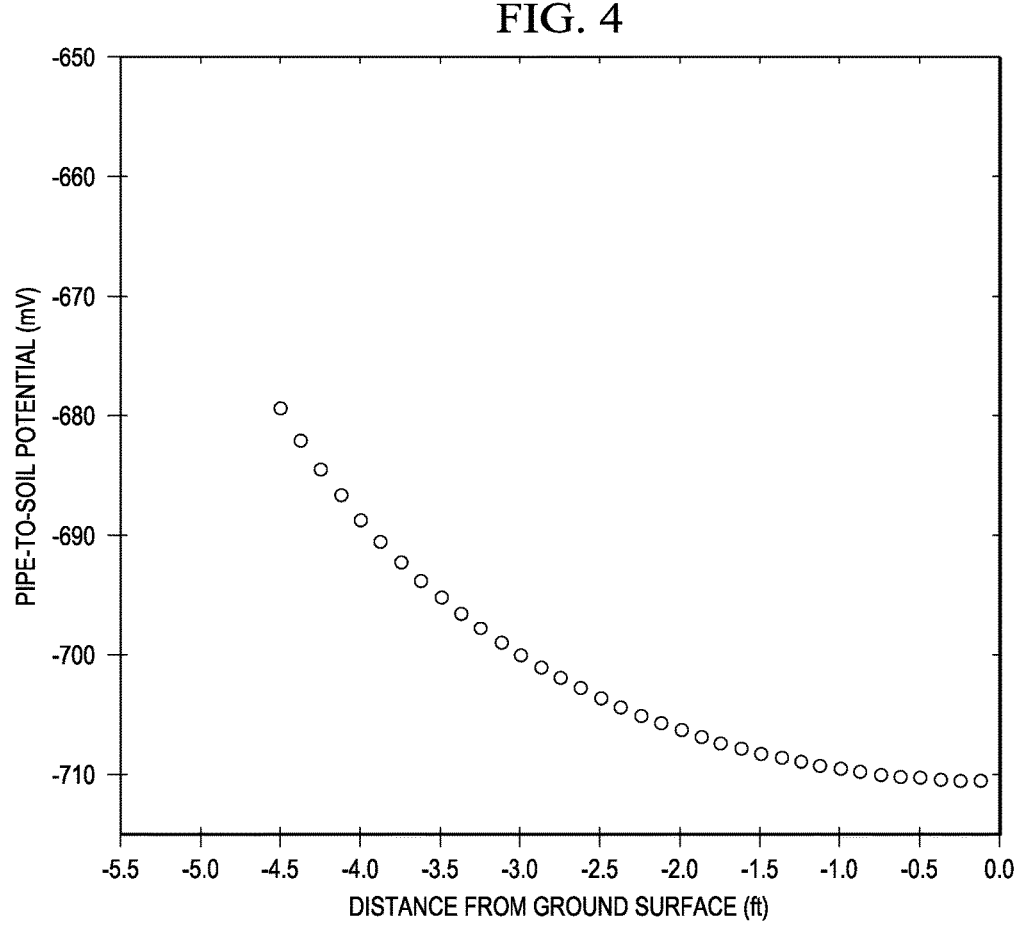
FIG. 4 illustrates vertically measured pipe-to-soil potential as a function of soil depth toward the pipeline.

FIG. 4 illustrates pipe-to-soil potential measurements obtained by probe 20 using the system of FIG. 3. Measurements have been obtained near a location of interest on a buried pipeline under cathodic protection. The measurement data is shown as a function of vertically measured distance (depth) from the ground surface.

In the example of this description, pipeline 11 is buried such that its top surface is 5.5 feet from the ground surface. As shown in FIG. 4, measurement data has been collected downward 4.5 feet from the ground surface in increments of 0.5 feet.

Once the pipe-to-soil potential versus depth data has been collected, the data is extrapolated to determine the potential at the top surface of the pipeline. In the example of this description, the pipe-to-soil potential data is extrapolated 1 foot beyond the measured distance.

The following process is an example of a process for extrapolating pipe-to-soil potential data from the lowest point of the measurement data (here 4.5 feet) to the pipe surface:

1) A mathematical model for the buried pipeline under cathodic protection is developed. An example of a suitable model is one developed using a boundary element method.

2) A mathematical function is derived using the mathematical model. This function may have the form of $\Sigma A_i \exp(B_i x)$. The values $A_i$ and $B_i$ are fitting constants, and x is the distance along the drilled hole from the pipe surface in units of feet.

3) The mathematical function is fitted to the pipe-to-soil potential data using a least square formulation.

4) The mathematical function is weighted with the measured data, such as by using a least square formulation.

5) The fitting constants $A_i$ and $B_i$ are used to extrapolate the pipe-to-soil potential data to the pipe surface.

The above-described extrapolation method also accounts for random noise that is likely to be present in pipe-to-soil potential measurements. The random noise effect is accounted for by using a weighting strategy in which measured data are used as weights in the least square formulation to obtain the fitting parameters.

As explained below, extrapolated potential data is used to calculate the gradient of the pipe-to-soil potential at the outer surface of the pipe wall at the defect location.

Corrosion Rate Calculation

The corrosion rate calculation is based on a differential form of Ohm's law. The slope of the potential near the pipe surface is dependent on the current generated due to corrosion reactions at the pipe surface, and is related to the current generated at the pipe surface according to the following equation:

$$i_{pipe} = -\kappa(\vec{n}\cdot\nabla\Phi)_{pipe}$$

In the above equation, $i_{pipe}$ is the current density at the pipe surface, $\kappa$ is the conductivity of the soil, $\check{n}$ is a dimensionless unit vector normal to the current generating surface, and $\Phi$ is the pipe-to-soil potential in the soil at the surface of the pipe under the probe. From this equation, if the gradient of the pipe-to-soil potential near the pipe surface and soil conductivity are known, a value of $i_{pipe}$ can be estimated.

More specifically, the extrapolated data, representing the potential at the surface of the pipeline, is first used to calculate the gradient of pipe-to-soil potential at the pipeline surface.

Soil conductivity measurements are conducted using commercially available soil conductivity testers. If there is a variation in soil conductivity, the soil conductivity is measured near the pipe surface. The gradient of the pipe-to-soil potential is multiplied by the measured soil conductivity to obtain the current density generated at the pipe surface.

Current density is proportional to the corrosion rate, and may be converted to a corrosion rate using Faraday's law. A Monte-Carlo simulation method may further be used to obtain an uncertainty range in the corrosion rates.

What is claimed is:

1. A method of using a vertical probe for collecting corrosion data from a location of interest on a pipeline buried in soil, the pipeline being under cathodic protection, comprising:

drilling a vertical hole in the soil such that the hole is drilled into the ground above the location of interest, and such that its axis is perpendicular or close to perpendicular to the location of interest, and to a depth approaching but not reaching the pipeline;

placing a probe in the hole, the probe having a vertical rail, a slider attached to the rail and moveable along the length of the rail, a single reference electrode attached to the slider, a ruler also attached to the slider;

wherein the reference electrode and the ruler move with the slider and the ruler indicates the depth of the reference electrode;

positioning the reference electrode at a first position along the rail, thereby positioning the reference electrode at a first depth above the location of interest;

measuring the structure-to-soil electric potential at the first depth;

re-positioning, without removing the probe from the hole, the reference electrode to a second position along the rail, thereby positioning the reference electrode at a second depth at relative to the same location of interest;

measuring a second structure-to-soil potential at the second depth; and repeating the re-positioning and subsequent measuring steps at least three times at varying depths until a data set representing the structure-to-soil potential at the varying depths relative to the same location of interest, over a distance of multiple feet, of the single reference electrode, to a predetermined depth not reaching the pipeline is obtained.

2. The method of claim 1 wherein the location of interest has a coating defect.

3. The method of claim 2 wherein the defect is a holiday in the coating of the pipeline.

4. The method of claim 2 wherein the defect is a disbondment in the coating of the pipeline.

5. The method of claim 1 wherein the pipeline is uncoated.

* * * * *